United States Patent [19]
Mirza

[11] Patent Number: 5,968,061
[45] Date of Patent: Oct. 19, 1999

[54] ENDOSCOPIC SURGICAL INSTRUMENT FOR THE IMPLEMENTATION OF ENDOSCOPIC SURGICAL PROCEDURES

[75] Inventor: M. Ather Mirza, St. James, N.Y.

[73] Assignees: Theodor Esser, Stony Brook; Eugene T. King, East Northport, both of N.Y.

[21] Appl. No.: 09/067,859

[22] Filed: Apr. 27, 1998

[51] Int. Cl.⁶ ..................................................... A61B 17/32
[52] U.S. Cl. ........................ 606/170; 606/172; 606/108; 604/171; 604/283
[58] Field of Search ...................................... 606/170, 172, 606/108, 104, 191, 192; 70/63, 466; 292/1.5; D8/331; 600/125, 127, 129, 131; 604/171, 283

[56] References Cited

U.S. PATENT DOCUMENTS

| | | | |
|---|---|---|---|
| 5,323,765 | 6/1994 | Brown | 606/170 |
| 5,334,212 | 8/1994 | Karell | 606/172 |
| 5,366,465 | 11/1994 | Mirza | 660/170 |
| 5,685,853 | 11/1997 | Bonnet | 600/131 |

OTHER PUBLICATIONS

Depth Gauge, Fracture Appliances, No. 251, p. 33, Feb. 1, 1947.

*Primary Examiner*—Michael Buiz
*Assistant Examiner*—Lien Ngo
*Attorney, Agent, or Firm*—Scully, Scott, Murphy & Presser

[57] ABSTRACT

Endoscopic surgical instruments in which provision is made for a locking device for a depth gauge or knife and sleeve arrangement which is adapted to be positioned on an endoscope, which provides for latching attachment thereto, and includes stop structure so as to enable the insertion thereof into a slotted cannula to a predetermined depth.

12 Claims, 5 Drawing Sheets

ENDOSCOPIC SURGICAL INSTRUMENT FOR THE IMPLEMENTATION OF ENDOSCOPIC SURGICAL PROCEDURES

BACKGROUND OF THE INVENTION

1. Field of the Invention

The present invention relates to an endoscopic surgical instrument for implementing endoscopic surgical procedures on a patient, and more particularly, is directed to a novel and unique instrument for performing endoscopic surgical procedures including such as uniportal plantar fascia release, lateral release for patella realignment, release of the posterior and other compartments of the leg, forearm fascial release for fascial compartment syndrome, and uniportal palmar subligmentous endoscopic carpal tunnel release, also referred to as distal single incision. Other potential types of surgery which can be implemented with the inventive endoscopic surgical instrument may include, but are not necessarily limited to, are ENT procedures, abdominal, gynecological, and genito-urinary procedures. The invention is also particularly directed to the provision of a unique endoscopic surgical instrument in the form of a slotted cannula incorporating a novel locking device for an endoscopic instrument and for the surgical cutting element, such as a knife blade or rasp; and selectively, a depth gauge including calibrating structure for measuring the length or depth of intended surgical procedure. Also shown is calibrating structure for the endoscopic knife; and a stop device for use with the endoscopic knife and/or the depth gauge, and which is adapted to be employed in the implementation of the foregoing method of endoscopically effecting the above-referenced surgical procedures.

In particular, although initially described herein as being directed to the above-mentioned aspect of implementing an endoscopic surgical procedure, numerous other surgical procedures may be readily implemented employing the inventive endoscopic surgical instrument as mentioned hereinbelow.

Basically, improved endoscopic surgical procedures and endoscopic instruments are disclosed and directed to the implementation of endoscopic carpal tunnel release and other surgical applications; as set forth in Mirza U.S. Pat. No. 5,366,465, issued Nov. 22, 1994, and U.S. Pat. No. 5,578,051, issued Nov. 26, 1996, the disclosures of which are incorporated herein by reference.

For purposes of illustration, the invention is described with regard to the implementation of an endoscopic surgical procedure in the treatment of carpal tunnel syndrome, this being only exemplary in nature and not limited thereto.

Carpal tunnel syndrome is usually characterized by numbness in the thumb, index, middle and ring fingers resulting from pressure being exerted on the median nerve inside the carpal tunnel, interfering with the function of such median nerve. This may readily manifest itself as a pain radiating as far as the shoulders and neck of the patient, resulting in impaired grasping ability by the hand and loss of sleep. This physical phenomenon is commonly the result of repetitive work and motions being carried out with the hand over lengthy periods of time, and is experienced by more ever younger people.

In essence, the carpal tunnel is formed by an arch of the eight wrist bones, spanned on its palmar surface by the transverse carpal ligament, the flexor retinaculum. The carpal tunnel functions as a large mechanical pulley to provide the appropriate moment arms for the digital flexor tendons as they pass through the tunnel. The tendons can then transmit force out into the fingers and impart only an appropriate amount of tension to develop torque at the level of the wrist.

Within the carpal tunnel, these tendons are lubricated and nourished by two synovial membranes—the radial and the ulnar bursa. The median nerve also shares the carpal tunnel, then branches out to provide sensory innervation to the palmar surfaces of the thumb, index, long and a portion of the ring finger. In addition, a small motor branch of the median nerve supplies the thenar muscles, which are responsible for lifting the thumb into opposition with the fingers.

Currently, a considerable array of methods or surgical techniques, and suitable therewith correlated surgical instruments, are being employed for purposes of implementing surgical procedures in effectuating carpal tunnel release in patients, and are generally designed for particular and highly specialized applications in this medical technology.

The customary procedure in implementing carpal tunnel release has heretofore been the forming of a lengthy incision, up to 8 cm in length across the palm from the wrist to the middle thereof, resulting in an unsightly scar, requiring division of all anatomical structures between the skin and the flexor retinaculum; i.e. the transverse carpal ligament. This created the potential for inadvertently cutting or injuring the palmar cutaneous nerve. Moreover, the patent normally encountered significant postoperative pain and discomfort, weakness of grip and pinch strength because of pillar infraction and the excessively lengthy extent of the incision. Such open surgery not only normally left the patient with a cosmetically unsightly scar extending from the wrist to the center of the palm, as mentioned hereinbefore, but also necessitated a lengthy and painful convalescence for the patient, whereby this convalescent period frequently caused the hand to be incapable of any significant physical work or manipulation for many weeks and even months, thereby effectively rendering the patient incapable of carrying out any meaningful work with the operated on hand and resulting in considerable financial losses being sustained by the patient.

Among more recent developments and advances in such surgical procedures, arthroscopic surgery employing the use of endoscopic devices has found widespread application, among others in connection with carpal tunnel release, in that in comparison with earlier customary surgical methods, any incisions necessary for such endoscopic/arthroscopic surgical procedures have been considerably reduced in size, thereby alleviating potential postoperative complications and pain encountered by the patient, while reducing any scarring to cosmetically desirable levels. Among various types of surgical procedures, techniques involving approaches by means of arthroscopic and endoscopic systems to carpal tunnel surgery have been acknowledged as being superior in providing significant advances over earlier so-called open surgical procedures necessitating large incisions. Such endoscopic surgical procedures have found widespread acceptance in effectuating carpal tunnel release for the purpose of alleviating the symptoms in a patient caused by carpal tunnel syndrome, also referred to as tardy median nerve palsy, normally caused by the compression of the median nerve within the carpal tunnel.

More recently, consideration has been given towards extending the scope of the endoscopic surgical procedure to other aspects such as plantar fascia release associated with heel spur syndrome in which a patient encounters severe pain at the bottom of the foot. This aspect, which is caused by the dense fibrous band of tissue which is known as the plantar fascia, is that a disorder of the foot, such as a structural misalignment, can cause an inflammation and result in intense pain in the foot. Although in many instances therapy may remedy the problems which are encountered, at times surgery is necessary in order to alleviate the problems.

These more recent endoscopic surgical approaches to remedying varying types of surgical problems afforded desirable alternatives to such earlier open surgical procedures, and especially when applied to effectuating carpal tunnel release, have found widespread favor with surgeons and patients in comparison with the earlier surgical methods which primarily constituted complex open surgical procedures, and which involved lengthy and painful post-operative convalescent periods.

2. Discussion of the Prior Art

Among numerous publications which describe recent advances in endoscopic surgical methods and instruments employed in connection therewith, particularly such as may be employable for carpal tunnel release procedures, there may be found the Agee carpal tunnel release system as disclosed in Agee, et al. U.S. Pat. Nos. 4,963,147 and 5,089,000, both of which disclose endoscopic surgical instruments and surgical procedures implemented therewith, which when applied to carpal tunnel release through an effective severing of the flexor retinaculum, or transverse carpal ligament, are adapted to provide relief to the patient. However, the instrument and methods developed by Agee, et al. as described in those publications, although superior to open surgery, inhibit readily unobstructed visualization of the surgical site during the sequence of severing the flexor retinaculum and do not provide adequate control in the manipulation of the instrument so as to reduce the inherent danger of damage to surrounding nerves and tissue to an acceptable minimum, and additionally necessitate the forming of two entry portals or incisions in the wrist and hand. Moreover, the endoscopic instruments developed in Agee, et al. are relatively cumbersome and expensive, requiring the surgeon to always use both of his hands, and necessitate the use of a swivel cutting blade construction operable independently of a viewing scope, which does not always provide the appropriate visualization during cutting of the flexor retinaculum so as to potentially present the danger of causing damage to adjacent or contiguously located tissue or nerves relative to the operating site, which could lead to serious and possibly permanent injury to the patient.

Another surgical system and instrument providing for an advanced technique over Agee, et al., which is particularly adapted for carpal tunnel release through the intermediary of an endoscopic surgical procedure is disclosed in Chow U.S. Pat. No. 5,029,573. However, in that instance, although setting forth a considerable advance over the methodology disclosed in the Agee, et al. U.S. patents, the surgical procedure employed by Chow requires the formation of two entry and exit portals or incisions, one in the wrist area and one in the palm, and the passage of an endoscopic medical instrument, such as an obturator through a considerable length beneath the subcutaneous areas of the palm of the patient. Again, the necessity for two widely separated incisions or entry portals, and the requirement for inserting a scope from one end of the instrument from one portal and with the instrument extending outwardly from the other portal or incision, while surgically severing or cutting through the flexor retinaculum or transverse carpal ligament from the other portal or incision, engenders a considerable obstruction toward a clear nonproblematic visualization of the operating site during the severing of the transverse carpal ligament and, once again, raises the specter of a potential risk of causing injury to tissue and nerves adjacent the operating site, especially such as to the median nerve, which could lead to serious permanent injury to a patient and possibly require additional corrective surgery necessitating subjecting the entire surgical or operating site to open surgery. Moreover, Agee, et al. and Chow require the surgeon to simultaneously employ both hands during the surgical procedures, thus necessitating the utilization of an unusually high degree of dexterity in manipulating the various components of the endoscopic surgical instruments.

Another method of endoscopic surgery and instrument for implementing surgery, particularly for the release of the carpal tunnel, are disclosed in Brown U.S. Pat. No. 5,323, 765. Although Brown directs the endoscopic surgery towards alleviating the syndrome encountered with the carpal tunnel, as in the previously discussed publications, two separate incisions are required. Moreover, although Brown also briefly mentions the application of the surgery and instrument or apparatus to the treatment of the foot, particularly the plantar fascia, again there is no detailed explanation provided as to the method in which this is accomplished, and apparently this would also necessitate providing a plurality of separate incisions to implement the surgery.

More recently, as described in Mirza U.S. Pat. No. 5,366, 465, the foregoing limitations and potential drawbacks which are encountered in the previously mentioned prior art publications have been improved upon through a novel method of implementing endoscopic surgical procedures, and a unique and inventive endoscopic surgical instrument developed for accomplishing this purpose, which has proven itself to be especially suited for, but not limited to, the effectuation of carpal tunnel release. In essence, the Mirza patent is directed to the severing of the flexor retinaculum or transverse carpal ligament through an endoscopic surgical procedure in which there is effected, by means of a uniportal or single incision, a palmar subligmentous endoscopic carpal tunnel release technique. This surgical procedure only requires the formation of a single and relatively small entry portal or incision in the palm proximate the distal side of the flexor retinaculum, thereby reducing any postoperative symptoms of the patient with only a cosmetically appealing scar formed on the palm, while eliminating the need for a second portal or incision proximate the wrist of the patient; and concurrently avoiding injury to the palmar arch and branches of the median nerve. Moreover, the endoscopic instrument employed in implementing the surgical method utilizes a cutting device which is mounted on a scope insertable through a cannula which has been initially inserted to extend beneath the flexor retinaculum from the distal side of the flexor retinaculum or transverse carpal ligament, upon the formation of a passage beneath the flexor retinaculum, after hyperextending of the hand, by the preceding insertion and manipulation of a curved dissector. Thereafter, the dissector is removed and the cannula and an obturator which is contained therein are inserted through the incision into the previously formed passage beneath the flexor retinaculum. The cannula of the surgical instrument has the obturator withdrawn therefrom, and in place of the latter, a scope is inserted into the cannula which enables unhindered and unobstructed visualization of the operating site and of the flexor retinaculum.

The scope is then withdrawn from the cannula, and the same scope or another scope with a cutting blade mounted at the leading end thereof inserted into and advanced through the cannula towards the flexor retinaculum. Severing of the latter is then effected by the cutting blade while affording an unhindered view of the operating site through the scope, thereby resultingly dramatically reducing or even completely eliminating the risk of any injury being sustained by tissue and nerves in the vicinity of the operating site; for example, such as the median nerve. This particular unhindered visualization of the operating site also enables the surgeon to exercise an improved degree of control over the possibly single-handed manipulation of the endoscopic instrument and cutting blade.

The cannula of the endoscopic instrument, which contains the obturator which is initially employed to be advanced beneath the flexor retinaculum or transverse carpal ligament subsequent to withdrawal of the curved dissector, may be provided with lateral or sideways wing-like or flange-like protrusions of curvilinear configurations which, in conjunction with an upwardly curving tip of the obturator projecting forwardly of the leading end of the cannula, is adapted to displace any tissue, or such as the media nerve, out of the path of the obturator and cannula as is being advanced; in effect, through essentially a sideways or lateral "shoving" action, thereby preventing any potential damage to such displaced tissue and nerve during the subsequent cutting procedure by maintaining such tissue well out of the way. Moreover, the leading tip of the obturator by being curved slightly upwardly towards the lower surface of the flexor retinaculum is also adapted to remove or dislocate any possible tissue or fascia located close to the surface of the flexor retinaculum and to ensure that the cannula and, resultingly, the subsequently inserted cutting blade are located as closely as possible to the flexor retinaculum.

Although described hereinabove with regard to the effectuation of a carpal tunnel release, the inventive uniportal endoscopic surgical methods and instrument may be also be readily applied to other surgical procedures; for example, such as uniportal plantar fascia release, lateral release for patella realignment, release of the posterior and other compartments of the leg, and forearm fascia release for fascial compartment syndrome. To that effect, reference may be had to the disclosure of Mirza U.S. Pat. No. 5,578,051 which considerably expands the surgical field of applications of the previous Mirza patent and also incorporates additional features in the endoscopic surgical instrument.

The foregoing endoscopic surgical methods, particularly the uniportal surgical procedures and surgical instruments developed by the Mirza U.S. Pat. Nos. 5,366,465 and 5,578,051, the disclosures of which are incorporated herein by reference, although providing considerable advantages over the current state of the art, are still further simplified by providing an improved composite slotted cannula and dissector of unitary or integral construction which eliminates a need for the provision of a separate dissector or a separate obturator, thereby reducing the number of surgical steps in the implementation of the various procedures. A particular aspect of eliminating the separate dissector and obturator heretofore utilized resides also in the composite cannula and dissector which forms the passageway towards the surgical site enabling an improved control during insertion thereof, particularly in the carpal tunnel, and by reducing the surgical steps during the implementation of the procedure renders the entire operation less expensive and of shorter duration, so as to further minimize any potential discomfort to a patient.

SUMMARY OF THE INVENTION

In order to still further improve upon the foregoing endoscopic surgical instruments and the surgical procedures associated therewith, provision is made for a novel locking device for a knife and sleeve arrangement which is adapted to be positioned on an endoscope, which provides for latching attachment thereto, and includes stop structure so as to enable the insertion thereof into a slotted cannula to a predetermined depth.

Pursuant to another aspect of the invention, in lieu of a cutting knife being attached to the end of the sleeve which is adapted to be positioned over the endoscope and then inserted into the slotted cannula, there may be provided a suitable depth gauge for measuring the length of the insertion with the endoscopic knife. For this purpose, there may be also be provided a suitable stop device which is mountable on the sleeve for respectively the endoscopic cutting knife and the depth gauge, and which would also limit the insertion of the endoscopic device into the uniportal entry formed in the patient.

Pursuant to another aspect of the invention, the endoscopic element which is inserted into the slotted cannula and which has the knife instrument mounted thereon to perform the surgical procedure, as described in the aforementioned Mirza U.S. patents, may be optionally replaced by a rasp member or structure which is able to pull out a so-called "curtain" of tissue; for example, during a particular procedure employed to relieve carpal tunnel syndrome at the ulnar bursa where the latter attaches to the flexor retinaculum. The rasp element is adapted to scrape the undersurface of the flexor retinaculum and to remove tissue adhering thereto.

Provision is made herein for simple and extremely efficient endoscopic surgical procedures which are particularly adapted, in conjunction with the use of the novel endoscopic instrument, the latter of which, pursuant to a specific embodiment, may comprise a novel unitary or integrally-constructed composite cannula and dissector which eliminates the need for a separate dissector and obturator, thereby reducing the steps employed in the implementation of a carpal tunnel release through the severing of the flexor retinaculum while producing minimal or no postoperative pain and discomfort in the patient, with a shortened convalescent period and with the formation only of a small cosmetically attractive scar on the palm of the patient's hand. This aspect is also readily applicable to the endoscopic surgical procedures described with regard to the uniportal plantar fascia release, lateral release for patella realignment, release of the posterior and other compartments of the leg, and the forearm fascial release for fascial compartment syndrome as described hereinbelow.

Accordingly, the present invention is directed to a novel and unique method of implementing an endoscopic surgical procedure through a uniportal entry to an operating site by means of a novel endoscopic surgical instrument.

The present invention is further directed to an endoscopic surgical instrument comprising a unique composite slotted cannula and dissector with a novel scope-mounted cutting or blade element for implementing the endoscopic surgical procedure pursuant to the invention.

A further object of the invention resides in the provision of a novel endoscope mounted cutting element or knife which is arranged on the leading end of a sleeve positionable over the endoscope, and wherein the distal or rearward end of the sleeve is adapted to be extended into and positioned in a novel and inventive locking device for latching the sleeve thereto so as to enable the insertion thereof into a slotted cannula.

A still further object of the present invention resides in the provision of a depth gauge for measuring the contemplated cutting depth with an endoscopic knife, wherein the depth gauge is mounted on the leading end of the sleeve, the opposite end of which is attached to a novel locking device and which is also adapted for insertion into the slotted cannula.

Yet another object of the invention resides in the provision of a stop device which is mountable on the sleeve, the latter of which is calibrated, and with the sleeve selectively mounting either the depth gauge or the cutting knife or blade, and wherein the stop device is adapted to provide for depth gauging calibration for determining the depth of cutting with the endoscopic knife, or the application of a rasp member.

The present invention is also directed to an endoscopic surgical instrument comprising a composite integral unitary slotted cannula and dissector enabling the elimination of the need for the provision of a separate dissector and a separate obturator which will reduce the number of steps in implementing an endoscopic surgical procedure of the type described.

Moreover, the present invention is directed to an endoscopic surgical instrument of the type described, in which a scope which is adapted to be advanced through the composite slotted cannula and dissector located beneath the flexor retinaculum has a cutting device mounted on a calibrated sleeve to enable severing of the flexor retinaculum while being able to afford the surgeon an unobstructed visualization of the operating site, and avoiding damage or injury to the palmar arch and branches of the median nerve.

The present invention is also directed to uniportal endoscopic surgical instruments employing the unique composite slotted cannula and dissector structure incorporating the novel calibrated sleeve, gauge and stop structure, and unique locking device, which to a considerable extent will reduce the number of surgical steps and time required in implementing a surgical procedure while enhancing the precision thereof. The present invention is further directed to a novel instrument facilitating uniportal endoscopic surgical methods which may be readily applied to various types of surgical procedures in addition to the treatment of carpal tunnel syndrome.

BRIEF DESCRIPTION OF THE DRAWINGS

Reference may now be had to the following detailed description of preferred embodiments of the endoscopic surgical instrument constructed pursuant to the invention, and which enables a surgical procedure for the effectuation of carpal ligament or tunnel release on a patient by a transverse severing of the flexor retinaculum, taken in conjunction with the accompanying drawings; in which.

DETAILED DESCRIPTION

Figure 1:
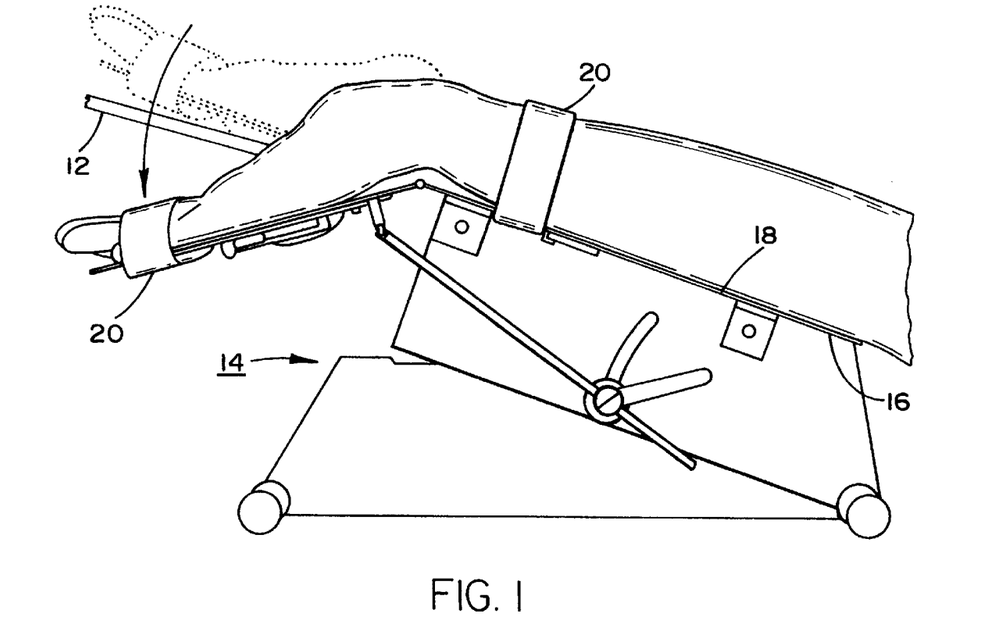
FIG. 1 illustrates a generally perspective view of the hand of a patient in a hyperextended position during a surgical procedure for effecting carpal ligament release, utilizing an endoscopic surgical instrument.

Reverting now in more specific detail to the description of the endoscopic surgical instrument as represented by the drawings, wherein FIG. 1 of the drawings illustrates a hand support 10 for an endoscopic system 12 which is employed, by way of example, for the procedure of effectuating the surgical release of a transverse carpal ligament; in essence, the severing of a flexor retinaculum in order to alleviate the symptoms and debilitating effects of carpal tunnel syndrome.

In this instance, the hand of a patient, shown with the endoscopic instrument 12, is supported on a handrest 14, which is in the form of a platform 16 having a planar upper surface 18 adjustable between an inclined or sloping and horizontal orientation enabling the lower arm portion of a patient to be supported thereon, and with straps 20 attached thereto for maintaining the hand of the patient in a hyperextended position in readiness for the endoscopic surgical procedure. A surgical support of this type is described in Esser U.S. Pat. No. 5,730,152; issued on Mar. 24, 1998; the disclosure of which is incorporated herein by reference.

As shown in FIG. 1 of the drawings, the endoscopic instrument 12 which is to be utilized for effectuating the carpal ligament release; in effect, the severing or transverse cutting through of the flexor retinaculum, is shown in the operative position thereof inserted through an incision into the hand of a patient.

Figure 2:
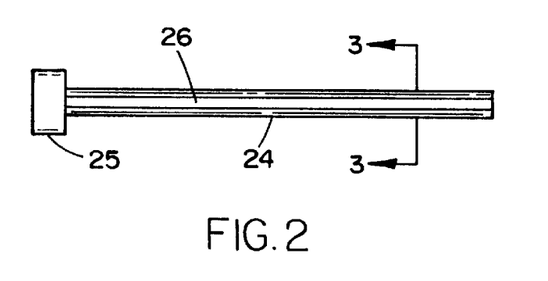
FIG. 2 illustrates a longitudinal top view of a slotted cannula of the endoscopic surgical instrument pursuant to the invention.
Figure 3:
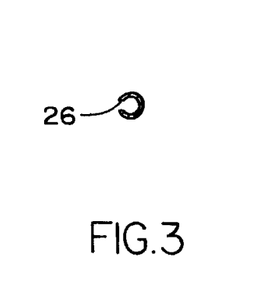
FIG. 3 illustrates a sectional view taken along line 3—3 in FIG. 2.

Referring to FIGS. 2 through 10, the endoscopic surgical instrument 10 comprises an arthroscope 22 which includes a cannula 24 having a through extending longitudinal slot 26 formed therein, and a knob or flange-like member 25 at one end thereof, as shown specifically in FIGS. 2 and 3 of the drawing.

The knob or member 25, as shown in the drawings, has a central aperture which is sized to facilitate passage therethrough with sufficient clearance of any obturator, scope and cutting element which is to be inserted into and withdrawn from the cannula 24 and which projects through longitudinal slot 26, as described in detail hereinbelow.

Figures 6, 7:
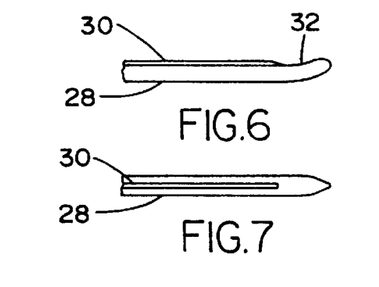
FIG. 6 illustrates a longitudinal side view of the leading end of an obturator adapted to be inserted into the slotted cannula of FIGS. 2 or 4.
FIG. 7 illustrates a top view of the leading end of the obturator.

An obturator 28, as in FIGS. 6 and 7, is adapted to be slidably received within the cannula, and presents a smooth outer surface through the intermediary of an axial, upstanding rib portion 30 which is engage able in close conformance within the longitudinal slot of the cannula upon insertion therein. The leading end of the obturator 28 is a tapered tip portion 32 which is bent upwardly in a direction towards the longitudinal rib to impart to the tip a somewhat upward curvature for a purpose to be described hereinbelow in more extensive detail. The leading end of the cannula may also be configured to form an integral obturator and dissector thereby eliminating separate components.

Figure 4:
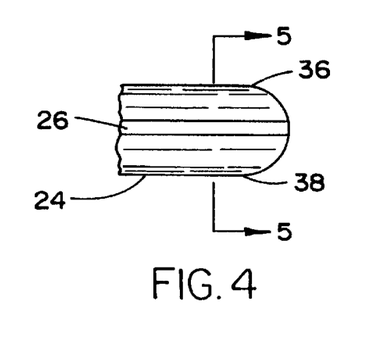
FIG. 4 illustrates a top view of the leading end portion of a modified slotted cannula.
Figure 5:
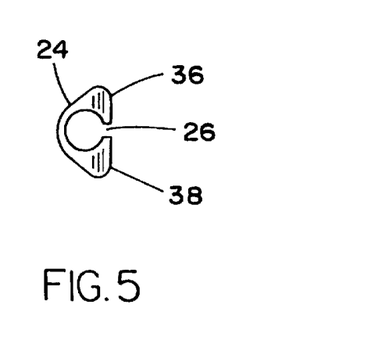
FIG. 5 illustrates a sectional view taken along line 5—5 in FIG. 4.

Although the cannula 24, as shown in FIGS. 2 and 3, is illustrated as being circular in crosssectional configuration along its external surface, pursuant to a modified embodiment, as shown in FIGS. 4 and 5, at opposite sides of the longitudinal slot 26, the outer surface of the cannula 24 may be equipped with integrally formed outwardly extending curvilinear flange portions 36 and 38 so as to essentially form so-called wings or fins, as described further on hereinbelow. These fin-like wings or flange portions 36 and 38 are integrally formed with the cannula and are also curved so that upon insertion of the obturator into the cannula, the tip end of the obturator essentially forms a smooth curvature at its juncture with the flanges 36 and 38.

Figure 8:
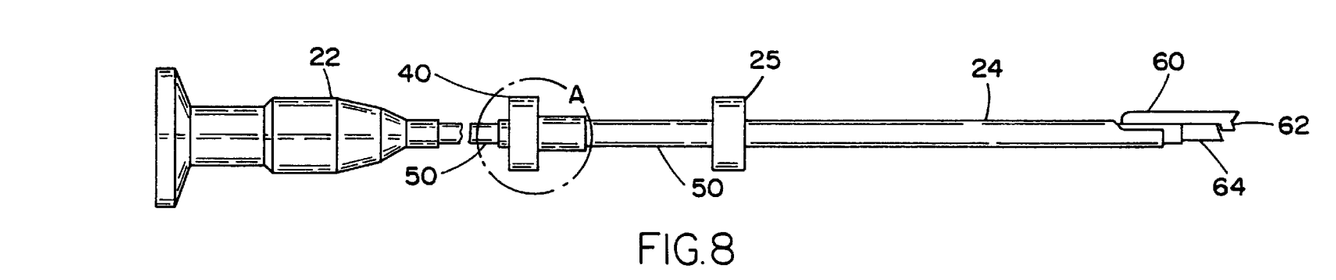
FIG. 8 illustrates a longitudinal side view of the endoscopic instrument, showing the scope and cutting device mounted on the latter inserted into the slotted cannula.
Figure 9:
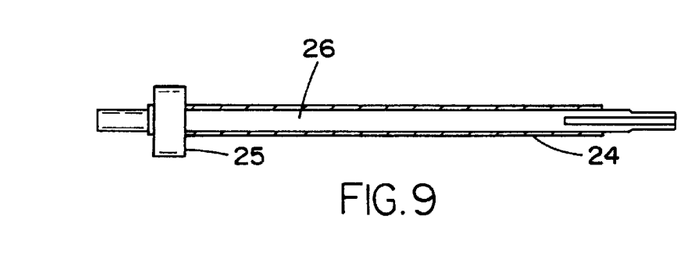
FIG. 9 illustrates a top view of the leading section of the endoscopic instrument shown in FIG. 8.
Figure 10:
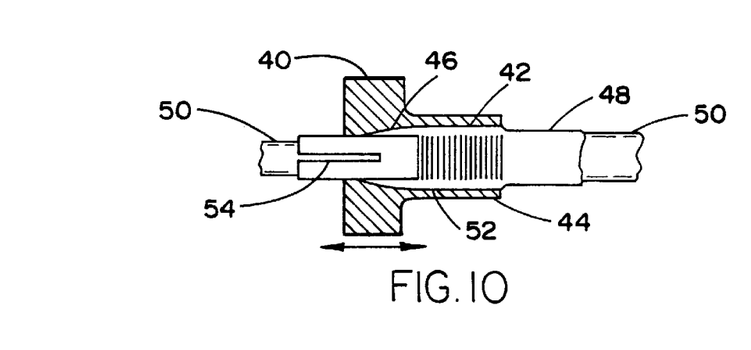
FIG. 10 illustrates, on a somewhat enlarged scale, a sectional view of the encircled portion 'A' of the instrument of FIG. 8.

As shown more specifically in FIGS. 8 through 10, the endoscopic instrument 10 is illustrated in its condition for cutting through the flexor retinaculum to effectuate carpal tunnel or ligament release.

Hereby, the arthroscope 22 includes a suitable knurled knob 40 having an internal threaded portion 42 in a cylindrical extension 44 and a tapered bore 46 for receiving a tubular knife or cutting blade holder 48.

The blade or knife holder 48 is adapted to receive a scope 50 of cylindrical configuration extending therethrough and lock the latter within the blade holder by simply axially displacing the knurled nut 40 through threaded interengagement between the internal thread 42 of the nut and an external thread 52 on the blade holder.

This will cause the tapered bore 46 of nut 40 to either compress the slotted portion 54 of the blade holder to clampingly engage the scope 50 or to loosen it so as to enable axial adjustment thereof relative to the blade holder.

A scope in the form of a rod member, in the absence of a blade holder, and which is connected to a video scanner (not shown) is adapted to be inserted through the cannula for effective visualization of the operative site.

In order to improve upon the structure of the endoscopic surgical instruments as disclosed in the applicants' earlier U.S. Pat. Nos. 5,366,465 and 5,578,051, the disclosures of which are incorporated herein by reference, pursuant to the present invention, in accordance with a specific feature there is provided a novel locking device for the attachment of either a cutting instrument or a depth gauge to an endoscopic rod element, whereby these components are adapted to be inserted into the slotted cannula.

As illustrated in the drawing FIGS. 11 through 14, the locking device 60 includes a rectangular housing structure 62, having a longitudinal through bore 64 for receiving a tubular element supporting a gauge or cutting blade and for receiving a rod-like endoscope. A pivotable lever 66 mounted on the housing structure 62 is adapted to be swung between an opened position to a locked position so as to impart a clamping action to a tubular element extending through bore 64 by means of a camming structure, as explained hereinbelow.

Figures 11, 12:
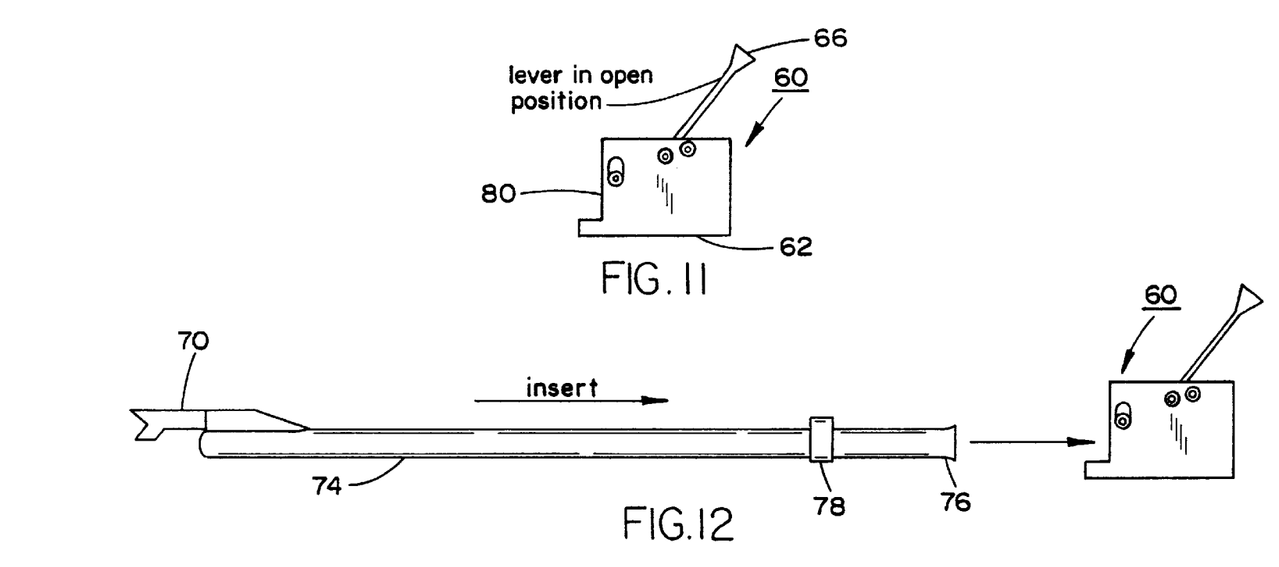
FIG. 11 illustrates a side view of the locking device of the invention.
FIG. 12 illustrates a tubular member mounting a surgical knife being inserted into the locking device.

Pursuant to the invention, a cutting instrument, such as a surgical knife 70, which may be disposable, as shown in drawing FIG. 12, is mounted at the leading end 72 of an elongate hollow tubular member 74 towards the opposite end of which the latter includes a hub portion 76 and a ring 78 spaced at a short distance therefrom, which forms a spacer defining the length of the tubular member 74 extending towards the knife blade 70, or any cutting or rasp instrument for removing tissue, such as a "curtain" of tissue, which is provided instead of the knife blade 70.

Figure 13:
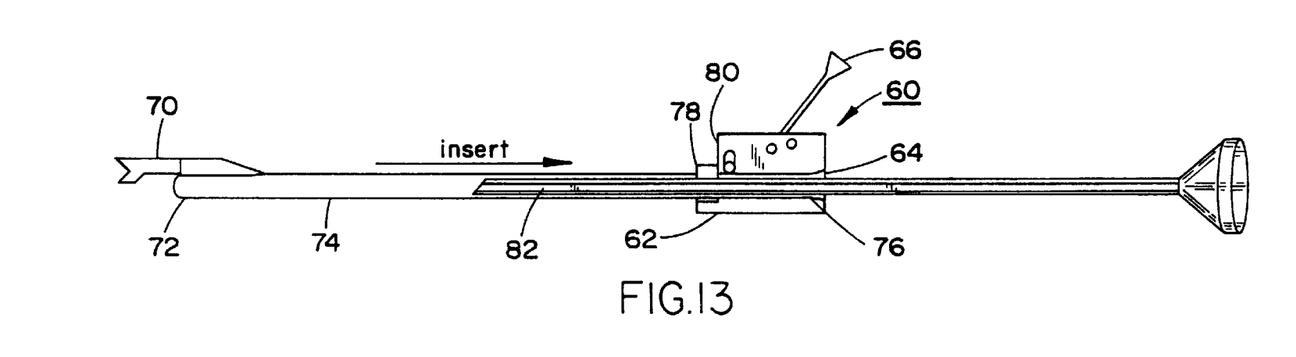
FIGS. 13 and 14 illustrate the assembling of the components including an endoscope.
Figure 14:
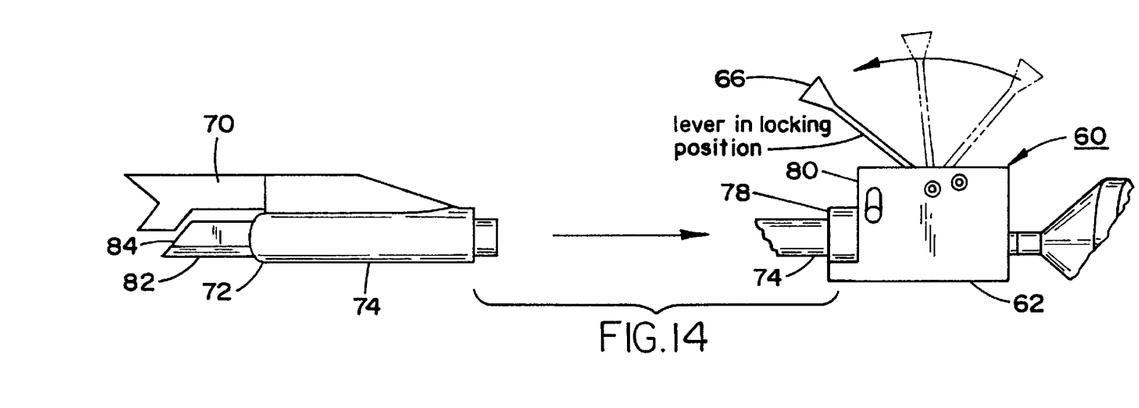

As shown in FIGS. 12 to 14, in diagrammatic sequence, the hub end portion 76 of the hollow tubular member mounting the cutting or rasp instrument or the knife 70 at the opposite end 72 is adapted to be positioned within the bore 64 formed in the locking device 60, and is inserted therein to the extent such that the spacer 78 ring which is fastened to the tubular member 74 comes into contact with the leading or forward surface 80 of the locking device 70. At that point in time, the endoscope 82 is advanced through the hollow tubular member 74 which mounts the cutting instrument or knife 70, as shown in FIG. 13, and the leading end 84 of the endoscope 82 positioned closely to the cutting blade or instrument 70, similar to the arrangements described in the above-mentioned earlier Mirza, U.S. Pat. Nos. 5,366,465 and 5,578,051.

As shown in FIG. 14, as the endoscope 82 has its leading end 84 appropriately positioned in proximity relative to the knife or cutting instrument 70, the lever 66 is pivoted forwardly into the locking position, thereby causing the endoscope 82 to be clamped to the tubular member 74 mounting the cutting element or blade 70. This will then facilitate ready insertion of the resultingly locked together components into the slotted cannula.

Figure 15:
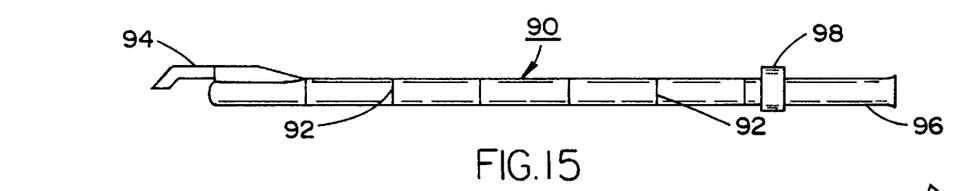
FIG. 15 illustrates the tubular member mounting a depth gauge.

The foregoing locking device 60 provides for a versatility not at all ascertainable in the technology, noting that the elongate tubular element 74 which mounts the knife or cutting element 70 at the leading end 72, may be calibrated along the length thereof so as to provide indication as to the depth to which the instrument is being introduced into the patient towards the surgical site. In this connection, in lieu of the tubular member mounting a knife or cutting element 70, prior to the use thereof with the endoscope 82, a tubular element 90 having calibrating markings 92 along the length thereof, which is similar to tubular element 74, may be equipped with a depth gauge 94 at the leading end thereof, as shown in FIG. 15, which, in a manner similar to the tubular member 74 mounting a knife or cutting element, is adapted to be inserted at the hub end 96 thereof into the locking device 60 until ring 98 contacts the locking device, with the endoscopic element inserted therein to provide illumination of the operating site, and the lever 66 being swung forwardly into the locking position.

Figure 16:
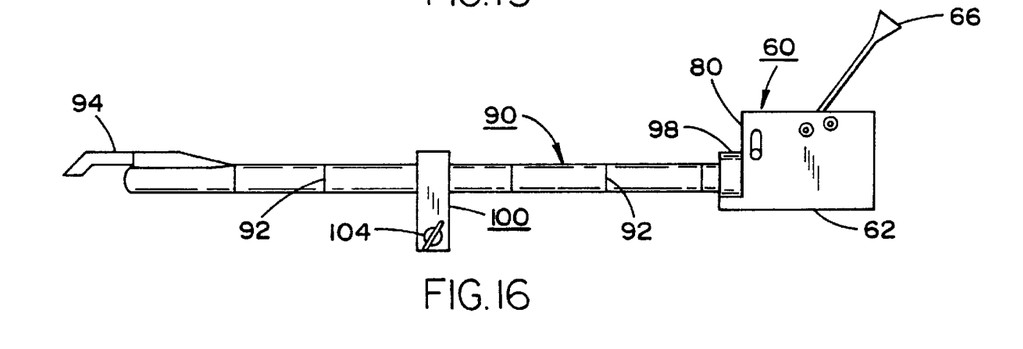
FIG. 16 illustrates the tubular member mounting the depth gauge connected to the locking device and having a stop device for limiting the extent of insertion into an incision formed in a patient.
Figure 17:
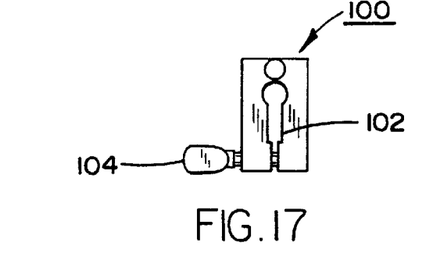
FIG. 17 is a sectional view taken along line 17—17 in FIG. 16.

Upon determination of the appropriate insertion depth to the surgical site by means of the tubular member 90 mounting the depth gauge 94, having the endoscope mounted therein, it is desirable to mount a stop device 100 in the form of a clamp member 102 on the tubular element 90 mounting the depth gauge 94, as shown in FIGS. 16 and 17, and tighten a clamping element 104, such as, for instance, a tightening screw, and which will provide information with regard to the cutting depth which is to be subsequently implemented, in that the stop device is positioned against or in proximity with the skin of the patient at the location of the incision, while the tubular element 90 and the endoscope therein are advanced within the cannula.

Upon withdrawing the tubular element 90 mounting the depth gauge 94 from the slotted cannula, a tubular element 74 mounting a knife or cutting element may be substituted therefor, as shown in the drawing FIGS. 12 to 14, and wherein the tubular member 74 or element mounting the knife or cutting instrument is similarly calibrated along its length. A stop device 100 is then fastened thereon at a location conforming with that of the stop device which was previously mounted on the calibrated tubular member 90 mounting the depth gauge 94. This will enable the precise determination of the depth to which the cutting instrument can be inserted through the cannula into the operating site, thereby preventing any injury due to any excessive penetration past the surgical site by the cutting instrument.

Figure 18:
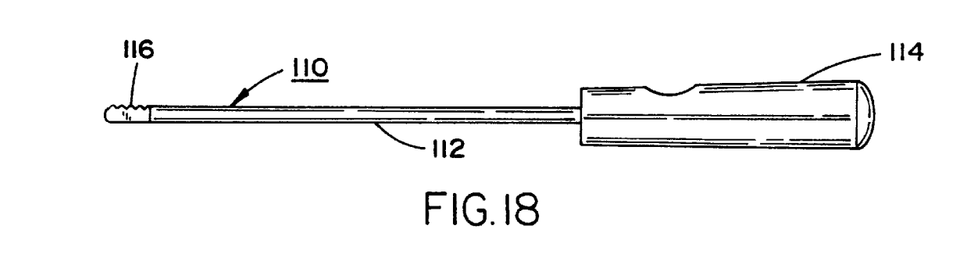
FIG. 18 illustrates a rasp member adapted to scrape a curtain of tissue at an operating site.
Figure 19:
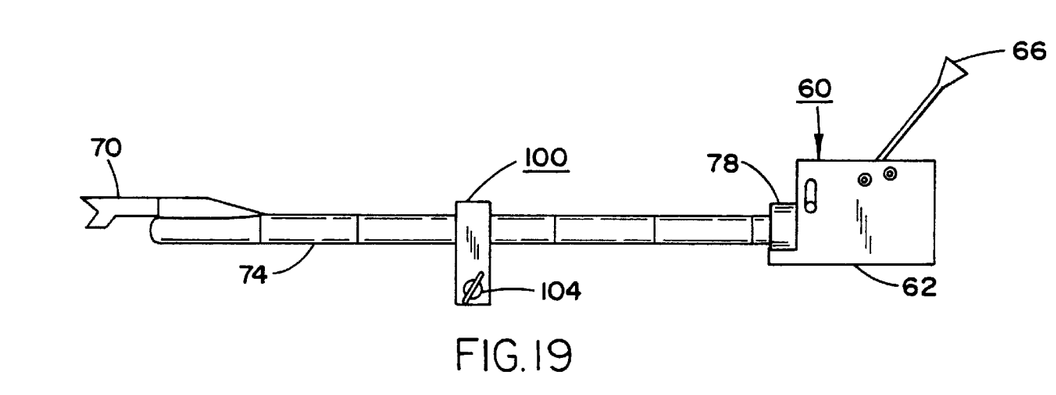
FIG. 19 is a view similar to FIG. 16, showing the tubular member mounting a cutting blade instead of a depth gauge.

Furthermore, in lieu of the use of a knife blade being mounted on a tubular member 74, as the cutting element there may also be employed a unique rasp member 110 having a plurality of transverse cutting edges formed thereon, and which is adapted to scrape tissue at the operating site. The rasp member 110, as shown in FIG. 18, may be in the form of a solid rod element 112, which is insertable into the cannula, including a gripping end 114 and having the rasp elements 116 at the leading end thereof for advance towards the operating site. Alternatively, the rasp may comprise rasp elements mounted on a hollow tubular element similar of the type which supports the depth gauge 94 or knife 70, and is adapted to be fastened to the locking device 60 and with an endoscope passed therethrough, with the lever 66 of the locking device thereafter locking the components into mutually fixed positions.

The foregoing novel structures provide further advantages in implementing the various endoscopic surgical procedures in conjunction with those described and claimed in the above-mentioned Mirza patents, and enable a more accurate gauging and positioning of the surgical instrument which are employed in implementing the procedures.

Quite apparently, by only slightly modifying the lengths and diameters of the inventive instrument, it is possible to customize, within the scope of the invention, the endoscopic surgical instrument so as to be adapted for numerous endoscopic surgical procedures of the type described herein.

While there has been shown and described what are considered to be preferred embodiments of the invention, it will, of course, be understood that various modifications and changes in form or detail could readily be made without departing from the spirit of the invention. It is, therefore, intended that the invention be not limited to the exact form and detail herein shown and described, nor to anything less than the whole of the invention herein disclosed as hereinafter claimed.

What is claimed is:

1. In an instrument for implementing an endoscopic surgical procedure at a selected operative site on a patient through an incision on said patient at a locale proximate said operative site to establish an entry portal; said instrument comprising an elongate cannula guide member including a longitudinal bore having open proximal and distal ends and an open slot extending along the length thereof communicating with said open ends, said cannula being advanceable a predetermined distance relative to said operating site and adapted to remain in place at said operating site during the implementing of the surgical procedure; an improvement comprising;

an elongate tubular member forming a sheath for an endoscopic viewing means being insertable into said cannula;

endoscopic viewing means comprising a rod-shaped element insertable into said elongate tubular member so as to extend to a leading end of said tubular member;

and locking means mountable on said tubular member proximate a rear end thereof for locking said endoscopic viewing means in said elongate tubular member, said locking means comprising a housing having a through-bore for extending the rear end of said tubular member therethrough, pivotable lever means being mounted on said housing; and camming means on said lever means for releasably latching said endoscopic viewing means to said tubular member responsive to pivoting positions of said lever means.

2. An instrument as claimed in claim 1, wherein said elongate tubular member includes a depth gauge mounted at the leading end of said tubular member.

3. An instrument as claimed in claim 2, wherein calibrating marks are provided on said elongate tubular member spaced along the length thereof.

4. An instrument as claimed in claim 2 or 3, wherein stop means are mountable on said elongate tubular member for determining the depth of insertion of said member relative to the operating site.

5. An instrument as claimed in claim 4, wherein said stop means comprises clamping means for fastening said stop means at predetermined locations along the length of said elongate tubular member.

6. An instrument as claimed in claim 5, wherein said elongate tubular member and the endoscopic viewing means fastened therein by said locking means is introduceable into said cannula to a depth determined by the position of said stop means on said tubular member.

7. An instrument as claimed in claim 2, wherein cutting means is mounted on the leading end of said elongate tubular member in lieu of said depth gauge.

8. An instrument as claimed in claim 7, wherein said cutting means comprises a knife blade.

9. An instrument as claimed in claim 7, wherein said cutting means comprises a rasp member.

10. An instrument as claimed in claim 1, wherein a rasp member is insertable into said cannula, said rasp member comprising an elongate rod having gripping means at one end and rasp elements formed at an opposite end thereof.

11. An instrument as claimed in claim 1, wherein said cannula has a dissector formed at the distal end thereof.

12. An instrument as claimed in claim 11, wherein said dissector is integrally constructed with said cannula so as to close the distal end of said cannula.

* * * * *